United States Patent
Stuart et al.

(10) Patent No.: US 8,670,017 B2
(45) Date of Patent: Mar. 11, 2014

(54) REMOTE PRESENCE SYSTEM INCLUDING A CART THAT SUPPORTS A ROBOT FACE AND AN OVERHEAD CAMERA

(75) Inventors: David Stuart, Santa Barbara, CA (US); Daniel Steven Sanchez, Summerland, CA (US); Fuji Lai, Goleta, CA (US); Kevin Hanrahan, Santa Barbara, CA (US); Charles S. Jordan, Santa Barbara, CA (US); David Roe, Santa Barbara, CA (US); James Rosenthal, Santa Barbara, CA (US); Amante Mangaser, Goleta, CA (US); Blair Whitney, Santa Barbara, CA (US); Derek Walters, Goleta, CA (US)

(73) Assignee: Intouch Technologies, Inc., Goleta, CA (US)

( * ) Notice: Subject to any disclaimer, the term of this patent is extended or adjusted under 35 U.S.C. 154(b) by 955 days.

(21) Appl. No.: 12/717,806

(22) Filed: Mar. 4, 2010

(65) Prior Publication Data

US 2011/0218674 A1    Sep. 8, 2011

(51) Int. Cl.
*H04N 7/15* (2006.01)
*G06F 17/00* (2006.01)
*G05B 15/00* (2006.01)

(52) U.S. Cl.
USPC ......... 348/14.05; 5/424; 219/137.2; 312/215; 348/14.08; 348/14.09; 375/240.12; 600/300; 600/301; 700/248; 700/253; 700/259; 702/150; 705/2; 706/11

(58) Field of Classification Search
USPC ......... 5/424; 219/137.2; 312/215; 348/14.05, 348/14.09, 14.08; 375/240.12; 600/300, 600/301; 700/259, 248, 253; 702/150; 706/11; 705/2
See application file for complete search history.

(56) References Cited

U.S. PATENT DOCUMENTS 3,821,995 A  7/1974  Aghnides
4,413,693 A  11/1983 Derby
(Continued)

FOREIGN PATENT DOCUMENTS

CA    2 289 697 A1    11/1998
CN    1554193 A       12/2004
(Continued)

OTHER PUBLICATIONS

Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.
(Continued)

*Primary Examiner* — Gerald Gauthier
(74) *Attorney, Agent, or Firm* — Chris Lambrecht

(57) ABSTRACT

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used in an operating room, wherein the overhead camera can be placed in a sterile field and the robot face can be used in a non-sterile field. The user at the remote station can conduct a teleconference through the robot face and also obtain a view of a medical procedure through the overhead camera.

30 Claims, 5 Drawing Sheets

(56) References Cited

U.S. PATENT DOCUMENTS

| | | |
|---|---|---|
| 4,471,354 A | 9/1984 | Smith |
| 4,519,466 A | 5/1985 | Shiraishi |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans et al. |
| 5,051,906 A | 9/1991 | Evans et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,224,157 A | 6/1993 | Yamada et al. |
| 5,231,693 A | 7/1993 | Backes et al. |
| 5,236,432 A | 8/1993 | Matsen, II et al. |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,350,033 A | 9/1994 | Kraft |
| 5,366,896 A | 11/1994 | Margrey et al. |
| 5,374,879 A | 12/1994 | Pin et al. |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,630,566 A | 5/1997 | Case |
| 5,636,218 A | 6/1997 | Ishikawa |
| 5,652,849 A | 7/1997 | Conway et al. |
| 5,657,246 A | 8/1997 | Hogan et al. |
| 5,659,779 A | 8/1997 | Laird et al. |
| 5,682,199 A | 10/1997 | Lankford |
| 5,684,695 A | 11/1997 | Bauer |
| 5,701,904 A | 12/1997 | Simmons et al. |
| 5,739,657 A | 4/1998 | Takayama et al. |
| 5,749,058 A | 5/1998 | Hashimoto |
| 5,749,362 A | 5/1998 | Funda et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,802,494 A | 9/1998 | Kuno |
| 5,836,872 A | 11/1998 | Kenet et al. |
| 5,838,575 A | 11/1998 | Lion |
| 5,857,534 A | 1/1999 | DeVault et al. |
| 5,867,653 A | 2/1999 | Aras et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,966,130 A | 10/1999 | Benman, Jr. |
| 5,973,724 A | 10/1999 | Riddle |
| 5,974,446 A | 10/1999 | Sonnenreich et al. |
| 5,995,884 A | 11/1999 | Allen et al. |
| 5,999,977 A | 12/1999 | Riddle |
| 6,006,946 A | 12/1999 | Williams et al. |
| 6,036,812 A | 3/2000 | Williams et al. |
| 6,133,944 A | 10/2000 | Braun et al. |
| 6,135,228 A | 10/2000 | Asada et al. |
| 6,148,100 A | 11/2000 | Anderson et al. |
| 6,170,929 B1 | 1/2001 | Wilson et al. |
| 6,175,779 B1 | 1/2001 | Barrett |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,321,137 B1 | 11/2001 | De Smet |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,381,515 B1 | 4/2002 | Inoue et al. |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Wang et al. |
| 6,468,265 B1 | 10/2002 | Evans et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |

(56) References Cited

U.S. PATENT DOCUMENTS

| | | |
|---|---|---|
| 6,580,246 B2 | 6/2003 | Jacobs |
| 6,584,376 B1 | 6/2003 | Van Kommer |
| 6,587,750 B2 | 7/2003 | Gerbi et al. |
| 6,594,269 B1 | 7/2003 | Polcyn |
| 6,594,552 B1 | 7/2003 | Nowlin et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,646,677 B2 | 11/2003 | Noro et al. |
| 6,650,748 B1 | 11/2003 | Edwards et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,958,706 B2 | 10/2005 | Chaco et al. |
| 6,965,394 B2 | 11/2005 | Gutta et al. |
| 6,995,664 B1 | 2/2006 | Darling |
| 7,030,757 B2 | 4/2006 | Matsuhira et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,129,970 B2 | 10/2006 | James et al. |
| 7,133,062 B2 | 11/2006 | Castles |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,171,286 B2 | 1/2007 | Wang et al. |
| 7,174,238 B1 | 2/2007 | Zweig |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai |
| 7,227,334 B2 | 6/2007 | Yang et al. |
| 7,256,708 B2 | 8/2007 | Rosenfeld |
| 7,262,573 B2 | 8/2007 | Wang et al. |
| 7,289,883 B2 | 10/2007 | Wang et al. |
| 7,292,912 B2 | 11/2007 | Wang et al. |
| 7,321,807 B2 | 1/2008 | Laski |
| 7,346,429 B2 | 3/2008 | Goldenberg et al. |
| 7,382,399 B1 | 6/2008 | McCall |
| 7,386,730 B2 | 6/2008 | Uchikubo |
| 7,432,949 B2 | 10/2008 | Remy et al. |
| 7,441,953 B2 | 10/2008 | Banks |
| 7,525,281 B2 | 4/2009 | Koyanagi et al. |
| 7,535,486 B2 | 5/2009 | Motomura et al. |
| 7,593,030 B2 | 9/2009 | Wang et al. |
| 7,624,166 B2 | 11/2009 | Foote et al. |
| 7,719,229 B2 | 5/2010 | Kaneko et al. |
| 7,761,185 B2 | 7/2010 | Wang et al. |
| 7,769,492 B2 | 8/2010 | Wang et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| RE42,288 E | 4/2011 | Degioanni |
| 7,924,323 B2 | 4/2011 | Walker et al. |
| 7,949,616 B2 * | 5/2011 | Levy et al. ............ 706/11 |
| 7,982,763 B2 | 7/2011 | King |
| 7,987,069 B2 * | 7/2011 | Rodgers et al. ............ 702/150 |
| 8,077,963 B2 | 12/2011 | Wang et al. |
| 8,116,910 B2 * | 2/2012 | Walters et al. ............ 700/259 |
| 8,170,241 B2 | 5/2012 | Roe et al. |
| 8,179,418 B2 * | 5/2012 | Wright et al. ............ 348/14.05 |
| 8,209,051 B2 | 6/2012 | Wang et al. |
| 8,292,807 B2 * | 10/2012 | Perkins et al. ............ 600/301 |
| 8,340,819 B2 * | 12/2012 | Mangaser et al. ............ 700/253 |
| 8,463,435 B2 * | 6/2013 | Herzog et al. ............ 700/248 |
| 2001/0002448 A1 | 5/2001 | Wilson et al. |
| 2001/0010053 A1 | 7/2001 | Ben-Shachar et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 * | 12/2001 | Barnett ............ 348/14.08 |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell |
| 2002/0027597 A1 | 3/2002 | Sachau |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0095238 A1 | 7/2002 | Ahlin et al. |
| 2002/0098879 A1 | 7/2002 | Rheey |
| 2002/0104094 A1 | 8/2002 | Alexander et al. |
| 2002/0111988 A1 | 8/2002 | Sato |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0030397 A1 | 2/2003 | Simmons |
| 2003/0048481 A1 | 3/2003 | Kobayashi |
| 2003/0050733 A1 | 3/2003 | Wang et al. |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0100892 A1 | 5/2003 | Morley et al. |
| 2003/0104806 A1 | 6/2003 | Ruef et al. |
| 2003/0114962 A1 | 6/2003 | Niemeyer |
| 2003/0126361 A1 | 7/2003 | Slater et al. |
| 2003/0135203 A1 | 7/2003 | Wang et al. |

(56) References Cited

U.S. PATENT DOCUMENTS

| | | |
|---|---|---|
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1* | 8/2003 | Kawakita ................ 375/240.12 |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0199000 A1 | 10/2003 | Valkirs et al. |
| 2003/0206242 A1 | 11/2003 | Choi et al. |
| 2003/0216834 A1 | 11/2003 | Allard |
| 2003/0220541 A1 | 11/2003 | Salisbury et al. |
| 2003/0220715 A1 | 11/2003 | William et al. |
| 2003/0231244 A1 | 12/2003 | Bonilla et al. |
| 2003/0232649 A1 | 12/2003 | Gizis et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1* | 4/2004 | James et al. ................ 348/14.09 |
| 2004/0088077 A1 | 5/2004 | Jouppi et al. |
| 2004/0093409 A1 | 5/2004 | Thompson et al. |
| 2004/0098167 A1 | 5/2004 | Yi et al. |
| 2004/0102167 A1 | 5/2004 | Shim et al. |
| 2004/0117065 A1 | 6/2004 | Wang et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0170300 A1 | 9/2004 | Jouppi |
| 2004/0172301 A1 | 9/2004 | Mihai et al. |
| 2004/0174129 A1 | 9/2004 | Wang et al. |
| 2004/0175684 A1 | 9/2004 | Kaasa et al. |
| 2004/0179714 A1 | 9/2004 | Jouppi et al. |
| 2004/0189700 A1 | 9/2004 | Mandavilli et al. |
| 2004/0201602 A1 | 10/2004 | Mody et al. |
| 2004/0215490 A1 | 10/2004 | Duchon et al. |
| 2004/0224676 A1 | 11/2004 | Iseki |
| 2004/0230340 A1 | 11/2004 | Fukuchi et al. |
| 2004/0240981 A1 | 12/2004 | Dothan |
| 2005/0003330 A1 | 1/2005 | Asgarinejad |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0083011 A1 | 4/2005 | Yang et al. |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0154265 A1 | 7/2005 | Miro et al. |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0232647 A1 | 10/2005 | Takenaka |
| 2005/0267826 A1 | 12/2005 | Levy et al. |
| 2005/0283414 A1 | 12/2005 | Fernandes et al. |
| 2006/0007943 A1 | 1/2006 | Fellman |
| 2006/0013263 A1 | 1/2006 | Fellman |
| 2006/0013469 A1 | 1/2006 | Wang et al. |
| 2006/0014388 A1 | 1/2006 | Wang et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1* | 3/2006 | Wang et al. .................... 600/300 |
| 2006/0052684 A1 | 3/2006 | Takahashi et al. |
| 2006/0064212 A1 | 3/2006 | Thorne |
| 2006/0074525 A1 | 4/2006 | Close et al. |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1* | 6/2006 | Meek et al. .................... 312/215 |
| 2006/0142983 A1 | 6/2006 | Sorensen |
| 2006/0161303 A1 | 7/2006 | Wang et al. |
| 2006/0164546 A1 | 7/2006 | Adachi et al. |
| 2006/0173712 A1 | 8/2006 | Joubert |
| 2006/0178776 A1 | 8/2006 | Feingold et al. |
| 2006/0189393 A1 | 8/2006 | Edery |
| 2006/0195569 A1 | 8/2006 | Barker |
| 2006/0259193 A1 | 11/2006 | Wang et al. |
| 2006/0293788 A1 | 12/2006 | Pogodin |
| 2007/0021871 A1 | 1/2007 | Wang et al. |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0112700 A1 | 5/2007 | Den et al. |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0135967 A1 | 6/2007 | Jung et al. |
| 2007/0142964 A1 | 6/2007 | Abramson |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0199108 A1 | 8/2007 | Angle et al. |
| 2007/0216347 A1 | 9/2007 | Kaneko et al. |
| 2007/0250212 A1 | 10/2007 | Halloran et al. |
| 2007/0262884 A1 | 11/2007 | Goncalves et al. |
| 2007/0273751 A1 | 11/2007 | Sachau |
| 2007/0291109 A1 | 12/2007 | Wang et al. |
| 2007/0291128 A1 | 12/2007 | Wang et al. |
| 2008/0011904 A1 | 1/2008 | Cepollina et al. |
| 2008/0065268 A1 | 3/2008 | Wang et al. |
| 2008/0082211 A1 | 4/2008 | Wang et al. |
| 2008/0133052 A1 | 6/2008 | Jones et al. |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0255703 A1 | 10/2008 | Wang et al. |
| 2008/0263451 A1 | 10/2008 | Portele et al. |
| 2008/0269949 A1 | 10/2008 | Norman et al. |
| 2008/0281467 A1 | 11/2008 | Pinter |
| 2009/0030552 A1 | 1/2009 | Nakadai et al. |
| 2009/0044334 A1* | 2/2009 | Parsell et al. .................... 5/424 |
| 2009/0055023 A1 | 2/2009 | Walters et al. |
| 2009/0105882 A1 | 4/2009 | Wang et al. |
| 2009/0125147 A1 | 5/2009 | Wang et al. |
| 2009/0237317 A1 | 9/2009 | Rofougaran |
| 2009/0240371 A1 | 9/2009 | Wang et al. |
| 2009/0259339 A1 | 10/2009 | Wright et al. |

(56) References Cited

U.S. PATENT DOCUMENTS

| | | |
|---|---|---|
| 2010/0010672 A1 | 1/2010 | Wang et al. |
| 2010/0010673 A1 | 1/2010 | Wang et al. |
| 2010/0019715 A1 | 1/2010 | Roe et al. |
| 2010/0051596 A1* | 3/2010 | Diedrick et al. ........... 219/137.2 |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0191375 A1 | 7/2010 | Wright et al. |
| 2010/0268383 A1 | 10/2010 | Wang et al. |
| 2010/0323783 A1 | 12/2010 | Nonaka et al. |
| 2011/0050841 A1 | 3/2011 | Wang et al. |
| 2011/0071702 A1 | 3/2011 | Wang et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0218674 A1* | 9/2011 | Stuart et al. ................... 700/259 |
| 2011/0245973 A1 | 10/2011 | Wang et al. |
| 2011/0292193 A1 | 12/2011 | Wang et al. |
| 2011/0301759 A1 | 12/2011 | Wang et al. |
| 2012/0023506 A1 | 1/2012 | Maeckel et al. |
| 2012/0072023 A1 | 3/2012 | Ota |
| 2012/0092157 A1 | 4/2012 | Tran |
| 2012/0191464 A1* | 7/2012 | Stuart et al. ....................... 705/2 |

FOREIGN PATENT DOCUMENTS

| | | |
|---|---|---|
| CN | 1554985 A | 12/2004 |
| CN | 101106939 A | 1/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 0 466 492 A2 | 1/1992 |
| EP | 92/488673 A2 | 6/1992 |
| EP | 09 81905 B1 | 2/2002 |
| EP | 1 262 142 A2 | 12/2002 |
| EP | 1 536 660 B2 | 9/2004 |
| EP | 1 536 660 A2 | 6/2005 |
| EP | 2005/1573406 A2 | 9/2005 |
| EP | 2005/1594660 A2 | 11/2005 |
| EP | 2007/1791464 A2 | 6/2007 |
| EP | 2007/1800476 A2 | 6/2007 |
| EP | 2007/1856644 A2 | 11/2007 |
| EP | 2008/1928310 A2 | 6/2008 |
| EP | 2009/2027716 A2 | 2/2009 |
| EP | 2010/2145274 A1 | 1/2010 |
| EP | 2010/2214111 A2 | 8/2010 |
| EP | 2010/2263158 A2 | 12/2010 |
| EP | 2011/2300930 A2 | 3/2011 |
| EP | 2011/2342651 A2 | 7/2011 |
| JP | 2007-213753 A | 8/1995 |
| JP | 2007-248823 A | 8/1995 |
| JP | 07-257422 A | 10/1995 |
| JP | 08-084328 A | 3/1996 |
| JP | 96/8320727 A | 12/1996 |
| JP | 9-267276 A | 10/1997 |
| JP | 10079097 A | 3/1998 |
| JP | 10288689 A | 10/1998 |
| JP | 2000-032319 A | 1/2000 |
| JP | 2000/049800 A | 2/2000 |
| JP | 2000/079587 A | 3/2000 |
| JP | 2000/196876 A | 7/2000 |
| JP | 2000-235423 A | 8/2000 |
| JP | 2001/125641 A | 5/2001 |
| JP | 2001-147718 A | 5/2001 |
| JP | 2001/179663 A | 7/2001 |
| JP | 2001/198865 A | 7/2001 |
| JP | 2001-198868 A | 7/2001 |
| JP | 2001-199356 A | 7/2001 |
| JP | 2000-188124 | 1/2002 |
| JP | 2002-000574 A | 1/2002 |
| JP | 2002-046088 A | 2/2002 |
| JP | 2002/101333 A | 4/2002 |
| JP | 2002/112970 A | 4/2002 |
| JP | 2002-305743 A | 10/2002 |
| JP | 2002-355779 A | 12/2002 |
| JP | 2004/524824 T | 8/2004 |
| JP | 2004/261941 A | 9/2004 |
| JP | 2004/2898379 A | 10/2004 |
| JP | 2005/028066 A | 2/2005 |
| JP | 2005/059170 A | 3/2005 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007/081646 A | 6/2007 |
| JP | 2010/064154 A | 3/2010 |
| JP | 2010/532109 A | 9/2010 |
| JP | 2010/246954 A | 11/2010 |
| KR | 2006/0037979 A | 5/2006 |
| KR | 2009/0012542 A | 2/2009 |
| KR | 2010/0019479 A | 2/2010 |
| KR | 2010/0139037 A | 12/2010 |
| WO | WO 93/06690 A1 | 4/1993 |
| WO | WO 98/51078 A | 11/1998 |
| WO | WO 99/67067 A1 | 12/1999 |
| WO | 00/33726 A3 | 6/2000 |
| WO | WO 03/077745 A | 9/2003 |
| WO | 2004/008738 A1 | 1/2004 |
| WO | 2004/012018 A2 | 2/2004 |
| WO | WO 2004/075456 A | 9/2004 |
| WO | 2006/012797 A1 | 2/2006 |
| WO | 2006/078611 A1 | 4/2006 |
| WO | WO 2007/041295 A2 | 9/2006 |
| WO | 2007/041295 A2 | 4/2007 |
| WO | 2007/041038 A1 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Bauer, et al., "Remote telesurgical mentoring: feasibility and efficacy", IEEE, 2000, pp. 1-9.
Brooks, "Remote Presence", Abstracts from Flesh & Machines, How Robots Will Change Us, Feb. 2002, pp. 131-147.
Davis, "Meet iRobot, The Smartest Webcam on Wheels," Wired Magazine, 8.09, http://www.wired.com/wired/archive/8.09/irobot_pr.html, Sep. 2000, 2 pgs.
Dean, et al., "1992 AAAI Robot Exhibition and Competition," AI Magazine, Spring 1993, 10 pgs.
"Defendant VGo Communications, Inc.'s Invalidity Contentions Pursuant to the Feb. 27, 2012 Civil Minute Order", May 2, 2012.
"Defendant-Counterclaimant VGo Communications, Inc.'s Supplemental Invalidity Contentions Pursuant to the Feb. 27, 2012 Civil Minute Order", May 14, 2012.
Dudenhoeffer, et al., "Command And Control Architectures For Autonomous Micro-Robotic Forces", http://www.inl.gov/technicalpublications/Documents/3157051.pdf, Apr. 2001.
Elhajj, "Real-Time Haptic Feedback in Internet-Based Telerobotic Operation", IEEE International Conference on Electro/Information

(56) References Cited

OTHER PUBLICATIONS

Technology, http://www.egr.msu.edu/~ralab-web/cgi_bin/internet-teleoperation.php, Jun. 2000.
Fong, "Collaborative Control: A Robot-Centric Model for Vehicle Teleoperation", The Robotics Institute Carnegie Mellon University, http:web.archive.org/web/200305040803/www.ricmu.edu/cgi-bin/tech_reports.cgi?year=2001&text=0, Nov. 2001.
Grow, "Office Coworker Robot," Time Magazine, http://www.time.com/time/specials/packages/article/0,28804,1936165_1936255_1936640,00.html, Nov. 19, 2001, 2 pgs.
ITU, "ITU-T H.281 A Far End Camera Control Protocol For Videoconferences using H.224", http://www.itu.int/rec/T-RECH.281-199411-I/en, Nov. 1994.
ITU, "ITU-T H.450.11 Call Intrusion Supplementary Service for H.323", http://www.itu.int/rec/T-RECH.450.11-200103-I/en, Mar. 2001.
ITU, "ITU-T H.450.9 Call Completion Supplementary Services for H.323", http://www.itu.int/rec/T-RECH.450.9-200011-I/en, Nov. 2000.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Metz, "HP Labs", PCMAG.com, http://www.pcmag.com/article2/0,2817,1130820,00.asp, Jul. 1, 2003.
"PictureTel Adds New Features And Functionality To Its Award-Winning Live200 Desktop Videoconferencing System", PR Newswire Association, LLC, Gale, Cengange Learning, http://www.thefreelibrary.com/PictureTel+Adds+New+Features+And+Functionality+To+Its+Award-Winning...-a019512804, Jun. 13, 1997.
Picturetel, "PictureTel Live200 for Windows NT Product Guide", http://support.polycom.com/global/documents/support/user/products/video/live200_live200NT_product_guide.pdf, Nov. 1994.
Roach, "Automatic Call Back Service in SIP", http://tools.ietf.org/pdf/draftroach-sip-acb-00.pdf, Mar. 2000.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
U.S. Appl. No. 10/783,760, filed Feb. 20, 2004, Wang, et al., 48 pgs.
U.S. Appl. No. 60/449,762, filed Feb. 24, 2003, Wang, et al., 28 pgs.
Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Zambroski, "CMU, Pitt Developing 'nursebot'", http://www.cs.cmu.edu/~nursebot/web/press/tribunereview.html, Oct. 27, 2000.
Al-Kassab, "A Review of Telemedicine", Journal of Telemedicine and Telecare, 1999, vol. 5, Supplement 1.
F. Ando et al., "A Multimedia Self-service Terminal with Conferencing Functions", 1995, IEEE, pp. 357-362.
Android Amusement Corp., "What Marketing Secret . . . Renting Robots from Android Amusement Corp!", (Advertisement) 1982.
Applebome, "Planning Domesticated Robots for Tomorrow's Household", New York Times, Mar. 4, 1982, pp. 21 and 23, http://www.theoldrobots.com/images17/dc17.JPG.
Baltus et al., "Towards Personal Service Robots for the Elderly, Proceedings for the Elderly Workshop on Interactive Robots and Entertainment", 2000, Computer Science and Robotics, http://www.cs.cmu.edu/thrun/papers/thrun.nursebot-early.pdf.
Bar-Cohen et al., Virtual reality robotic telesurgery simulations using MEMICA haptic system, Mar. 5, 2001, Internet, pp. 1-7.
Bartholomew, "An Apothecary's Pharmacy", 1230-1240 http://classes.bnf.fr/ema/grands/034.htm.
Bauer, Jeffrey C., "Service Robots in Health Care: The Evolution of Mechanical Solutions to Human Resource Problems", Jun. 2003.
Bauer, John et al., "Remote telesurgical mentoring: feasibility and efficacy", 2000, IEEE, pp. 1-9.

Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Apr. 16, 2002, Internet pp. 1-3.
Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.
Brooks, Rodney, Abstracts from Flesh & Machines, How Robots Will Change Us, "Remote Presence", p. 131-147, Feb. 2002.
Candelas Herias, F.A. et al., "Flexible virtual and remote laboratory for teaching Robotics", FORMATEX 2006, Proc. Advance in Control Education, Madrid, Spain, Jun. 21-23, 2006.
Celi et al., "The eICU: It's not just telemedicine", Critical Care Medicine, vol. 29, No. 8 (Supplement), Aug. 2001.
Cheetham, Anastasia et al., "Interface Development for a Child's Video Conferencing Robot", 2000, pp. 1-4.
Cleary et al., "State of the art in surgical robotics: Clinical applications and technology challenges", Feb. 24, 2002 Internet, pp. 1-26.
CNN, "Floating 'droids' to roam space corridors of the future", Jan. 12, 2000, Internet, pp. 1-4.
CNN.com/Technology, "Paging R.Robot: Machine helps doctors with patients", Sep. 30, 2003, Internet, 1-3.
Crowley, "Hello to Our Future", AARP Bulletin, Jan. 2000 http://www.cs.cmu.ed/-nursebot/web/press/aarp_99_14/millennium.html.
Dalton, "Techniques for Web Telerobotics", PhD Thesis, University of Western Australia, 2001, pp. 27-62, 149-191; http://telerobot.mech.uwa.edu.au/information.html, http://catalogue.library.uwa.edu.au/search.
Davies, "Robotics in Minimally Invasive Surgery", 1995, Internet, pp. May 1-2.
DiGiorgio, James, "Is Your Emergency Department of the 'Leading Edge'?", 2005, Internet, pp. 1-4.
Discovery Channel Canada, "Inventing the Future: 2000 Years of Discovery", Jan. 2, 2000 (Video/Transcript).
Elhajj et al., "Supermedia in Internet-based telerobotic operations", 2001, Internet, pp. 1-14.
Elhajj et al., "Synchronization and Control of Supermedia Transmission Via the Internet", Proceedings of 2001 International Symposium on Intelligent Multimedia, Video and Speech Processing, May 2-4, 2001, Hong Kong.
Ellison et al., "Telerounding and Patient Satisfaction Following Surgery".
Fels, "Developing a Video-Mediated Communication System for Hospitalized Children", Telemedicine Journal, vol. 5, No. 2, 1999.
Fetterman, "Videoconferencing over the Internet", 2001, Internet, pp. 1-8.
Fiorini, "Health Care Robotics: A Progress Report", IEEE International Conference on Robotics and Automation, pp. 1271-1276, Apr. 1997.
Ghiasi, "A Generic Web-based Teleoperations Architecture: Details and Experience", SPIE Conference on Telemanipulator and Telepresence Technologies VI, Sep. 1999.
Goldberg et al., "Collaborative Teleoperation via the Internet", IEEE International Conference on Robotics and Automation, Apr. 2000, San Francisco, California.
Goldberg, "Desktop Teleoperation via the World Wide Web, Proceedings of the IEEE International Conference on Robotics and Automation", 1995, pp. 654-659 http://citeseer.ist.psu.edu/cache/papers/cs/5/ftp:zSzzSzusc.eduzSzpubzSziriszSzraiders.pdf/gol.
Goldberg, "More Online Robots, Robots that Manipulate", Internet, Updated Aug. 2001 http://ford.ieor.berkeley.edu/ir/robots_a2.html.
Goldenberg, et al., "Telemedicine in Otolaryngology", American Journal of Otolaryngology, vol. 23, No. 1, 2002, pp. 35-43.
Goldman, Lea, "Machine Dreams", Entrepreneurs, Forbes, May 27, 2002.
Gump, Michael D., "Robot Technology Improves VA Pharmacies", 2001, Internet, pp. 1-3.

(56) References Cited

OTHER PUBLICATIONS

Han, et al., "Construction of an Omnidirectional Mobile Robot Platform Based on Active Dual-Wheel Caster Mechanisms and Development of a Control Simulator", 2000, Kluwer Acedemic Publishers, vol. 29, pp. 257-275.
Handley, "RFC 2327—SDP: Session Description Protocol", Apr. 1998 http://www.faqs.org/rfcs/rfc2327.html.
Hanebeck, "ROMAN: a mobile Robotic Assistant for Indoor Service Applications", Proceedings of the 1997 IEEE/RSJ International Conference on Intelligent Robots and Systems, 1997.
Harmo et al., "Moving Eye—Interactive Telepresence Over Internet With a Ball Shaped Mobile Robot", 2000.
Haule et al., "Control Scheme for Delayed Teleoperation Tasks", May 17, 1995, Proceedings of the Pacific Rim Conference on Communications, Computer and Signal Processing.
Hees, William P., "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
Ishiguro, "Integrating a Perceptual Information Infrastructure with Robotic Avatars: A Framework for Tele-Existence" Proceeding of IEEE Conference on Intelligent Robots and Systems, http://www.ai.soc.i.kyoto-u.ac.jp/services/publications/99/99conf/07.pdf.
Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.
Itu, "ITU-T H.323 Packet-based multimedia communications", ITU, Feb. 1998, http://www.itu.int/rec/T-REC-H.323-199802-S/en.
Ivanova, Natali, "Master's thesis: Internet Based Interface for Control of a Mobile Robot", Department of Numerical Analysis and Computer Science.
Jenkins, "Telehealth Advancing Nursing Practice", Nursing Outlook, Mar./Apr. 2001, vol. 49, No. 2.
Johanson, "Supporting video-mediated communication over the Internet", Chalmers University of Technology, Dept of Computer Engineering, Gothenburg, Sweden, 2003.
Jouppi, et al., "Mutually-Immersive Audio Telepresence", Audio Engineering Society Convention Paper, presented at 113$^{th}$ Convention Oct. 2002.
Jouppi, Norman P., "First Steps Towards Mutually-Immersive Mobile Telepresence", CSCW '02, Nov. 16-20, 2002, New Orleans LA.
Kanehiro, Fumio et al., "Virtual Humanoid Robot Platform to Develop Controllers of Real Humanoid Robots without Porting", 2001, IEEE, pp. 3217-3276.
Kaplan et al., "An Internet Accessible Telepresence".
Keller et al., "Raven Interface Project", Fall 2001 http://upclose.lrdc.pitt.edu/people/louw_assets/Raven_Slides.pps.
Khatib, "Robots in Human Environments", Proc. International Conference on Control, Automation, Robotics, and Vision, ICRACV2000, Dec. 2000, Singapore, pp. 454-457.
Kuzuoka et al., "Can the GestureCam Be a Surrogate?".
Lane, "Automated Aides", Newsday, Oct. 17, 2000, http://www.cs.cum.edu/-nursebot/web/press/nd4380.htm.
Lee et al., "A novel method of surgical instruction: International telementoring", 1998, Internet pp. 1-4.
Lim, Hun-ok et al., "Control to Realize Human-like Walking of a Biped Humanoid Robot", IEEE 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs (2004).
Loeb, Gerald, "Virtual Visit: Improving Communication for Those Who Need It Most", 2001.
Long, "HelpMate Robotics, Inc. (Formerly Transitions Research Corporation) Robot Navigation Technology", NIST Special Publication 950-1, Mar. 1999, http://www.atp.nist.gov/eao/sp950-1/helpmate.htm.
Luna, Nancy, "Robot a new face on geriatric care", OC Register, Aug. 6, 2003.
Mack, "Minimally invasive and robotic surgery", 2001, Internet IEEE, pp. 568-572.
Mair, "Telepresence—The Technology And Its Economic and Social Implications", IEEE Technology and Society, 1997.
Martin, Anya, "Days Ahead", Assisted Living Today, vol. 9, Nov./Dec. 2002, pp. 19-22.
McCardle et al., "The challenge of utilizing new technology in design education", 2000 Internet, pp. 122-127.
Meng et al., "E-Service Robot in Home Healthcare", Proceedings of the 2000 IEEE/RSJ, International Conference on Intelligent Robots and Systems, 2000, pp. 832-837.
Michaud, "Introducing 'Nursebot'", The Boston Globe, Sep. 11, 2001, pp. 1-5, http://www.cs.cmu.edu/nursebot/web/press/globe_3_01/index.html.
Mobile Robotics Research Group, "Mobile Robotics Research Group", 2000 Internet, pp. 1-2, Edinburgh.
Montemerlo, "Telepresence: Experiments in Next Generation Internet", CMU Robotics Institute, Oct. 20, 1998, http://www.ri.cmu.edu/creative/archives.htm (Video/Transcript).
Murphy, "Introduction to AI Robotics", 2000.
Nakajima et al., "A Multimedia Teleteaching System sing an Electronic Whiteboard for Two-Way Communication of Motion Videos and Chalkboards", 1993, IEEE, pp. 436-441.
"National Energy Research Scientific Computing Center, Berkeley Lab's RAGE Telepresence Robot Captures R&D100 Award", Jul. 2, 2002, http://www.nersc.gov/news/newsroom/RAGE070202.php.
Nomadic Technologies, Inc., "Nomad XR4000 Hardware Manual", Mar. 1999.
Ogata et al., "Emotional Communication Robot: WAMOEBA-2R—Emotion Model and Evaluation Experiments", 1999, Internet, pp. 1-16.
Ogata et al., "Development of Emotional Communication Robot: WAMOEBA-2r—Experimental evaluation . . . ", 2000 IEEE, pp. 175-180.
Oh et al., "Autonomous Battery Recharging for Indoor Mobile Robots", Proceedings of Australian Conference on Robotics and Automation, 2000, http://users.rsise.anu.edu.au/rsl/rsl_papers/ACRA2000/Auto_Recharge_Paper.pdf.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, "Designing Personal Tele-embodiment", IEEE International Conference on Robotics and Automation, 1998, http://www.prop.org/papers/icra98.pdf.
Paulos, Eric John, "Personal Tele-Embodiment", UC Berkeley, Fall 2001.
Paulos, "PRoP: Personal Roving Presence", ACM:CHI Proceedings of CHI '98, http://www.prop.org/papers/chi98.pdf.
Paulos, Video of PRoP 2 at Richmond Field Station, www.prop.org. May 2001, Printout of Home Page of Website and two-page Transcript of the audio portion of said PRoP Video.
Paulos, et al., "Ubiquitous Tele-embodiment: Applications and Implications", International Journal of Human Computer Studies, Jun. 1997, vol. 46, No. 6, pp. 861-877.
Pin et al., "A New Family of Omnidirectional and Holonomic Wheeled Platforms for Mobile Robots", IEEE, vol. 10, No. 4, Aug. 1994.
Rovetta et al., "A New Telerobotic Application: Remote Laparoscopic Surgery Using Satellites and Optical Fiber Networks for Data Exchange", Jun. 1, 1996, International Journal of Robotics Research, pp. 267-279.
Roy et al., "Towards Personal Service Robots for the Elderly", Internet, Mar. 7, 2002.
Salemi et al, "MILO: Personal robot platform", 2005, Internet, pp. 1-6.
Sandt, Frederic et al., "Perceptions for a Transport Robot in Public Environments", 1997, IROS '97.
Schaeffer, "Care-O-bot: A System for Assisting Elderly or Disabled Persons in Home Environments", Proceedings of AAATE-99, 1999,

(56) References Cited

OTHER PUBLICATIONS http://morpha.de/download/publications/IPA_Systems_For_AssistingElderly_or_DisabledPersons_AAATE1999.pdf.
Schulz, "Web Interfaces for Mobile Robots in Public Places", Robotics & Automation Magazine, IEEE, vol. 7, Issue 1, Mar. 2000.
Shimoga et al., Touch and force reflection for telepresence surgery, 1994, IEEE, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Spawar Systems Center, "Robart", 1998, San Diego, CA, http://web.archive.org/web/*/http://www.nosc.mil/robots/land/robart/robart.html http://web.archive.org/web/19981202205636/http://www.nosc.mil/robots/land/robart/robart.html.
Stephenson, Gary, "Dr. Robot Tested at Hopkins", Aug. 5, 2003, Internet, pp. 1-2.
Stoianovici et al., "Robotic Tools for Minimally Invasive Urologic Surgery", Dec. 2002, Internet, 1-17.
Suplee, "Mastering the Robot", The Washington Post, p. A01, Sep. 17, 2000 http://www.cs.cmu.edu-nursebot/web/press/wash/index.html.
Tahboub, Karim A. et al., "Dynamics Analysis and Control of a Holonomic Vehicle With Continously Variable Transmission", Mar. 2002, Journal of Dynamic Systems, Measurement, and Control, ASME vol. 124, pp. 118-126.
Tendick et al., "Human-Machine Interfaces for Minimally Invasive Surgery", 1997, IEEE, pp. 2771-2776.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", Nov. 2000, Internet, pp. 1-23.
Urquhart, Kim, "InTouch's robotic Companion 'beams up' healthcare experts", Medical Device Daily, vol. 7, No. 39, Feb. 27, 2003, p. 1, 4.
Weiss et al., Telework and video-mediated communication: Importance of real-time, interactive communication for workers with disabilities, pp. 1-4, California State University Northridge, http://www.csun.edu/cod/conf/1999/proceedings/session0238.html.
West et al., "Design of Ball Wheel Mechanisms for Omnidirectional Vehicles with Full Mobility and Invariant Kinematics", Journal of Mechanical Design, vol. 119, pp. 153-161, Jun. 1997.
Yamasaki et al., Applying Personal Robots and Active Interface to Video Conference Systems, 1995, Internet, pp. 243-248.
Yamauchi et al., PackBot: A Versatile Platform for Military Robotics, 2004, Internet, pp. 1-10.
Yong et al., "Robot task execution with telepresence using virtual reality technology", 1998, Internet, pp. 1-9.
Zamrazil, Kristie, "Telemedicine in Texas: Public Policy Concerns", House Research Organization Focus Report, Texas House of Representatives, No. 76-22, May 5, 2000 http://www.hro.house.state.tx.us/focus/telemed.pdf.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision/vision.html, Mar. 5, 1996.

\* cited by examiner

Robot Face
16

Overhead Camera

REMOTE PRESENCE SYSTEM INCLUDING A CART THAT SUPPORTS A ROBOT FACE AND AN OVERHEAD CAMERA

BACKGROUND OF THE INVENTION

1. Field of the Invention

The subject matter disclosed generally relates to the field of robotic tele-presence systems.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile tele-presence robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

InTouch also provides a system sold as VisitOR that includes a robot face that is attached to a boom. The boom and robot face can be installed into an operating room. Using a robot face in an operating room may require sterilization of the face. Additionally, the VisitOR requires the installation of a boom in the operating room. This can add to the cost and complexity of installing such a system.

BRIEF SUMMARY OF THE INVENTION

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone.

DETAILED DESCRIPTION

Disclosed is a tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used in an operating room, wherein the overhead camera can be placed above a sterile field to provide a more advantageous vantage point to view a procedure. The user at the remote station can conduct a teleconference through the robot face and also obtain a view of a medical procedure through the overhead camera.

Figure 1:
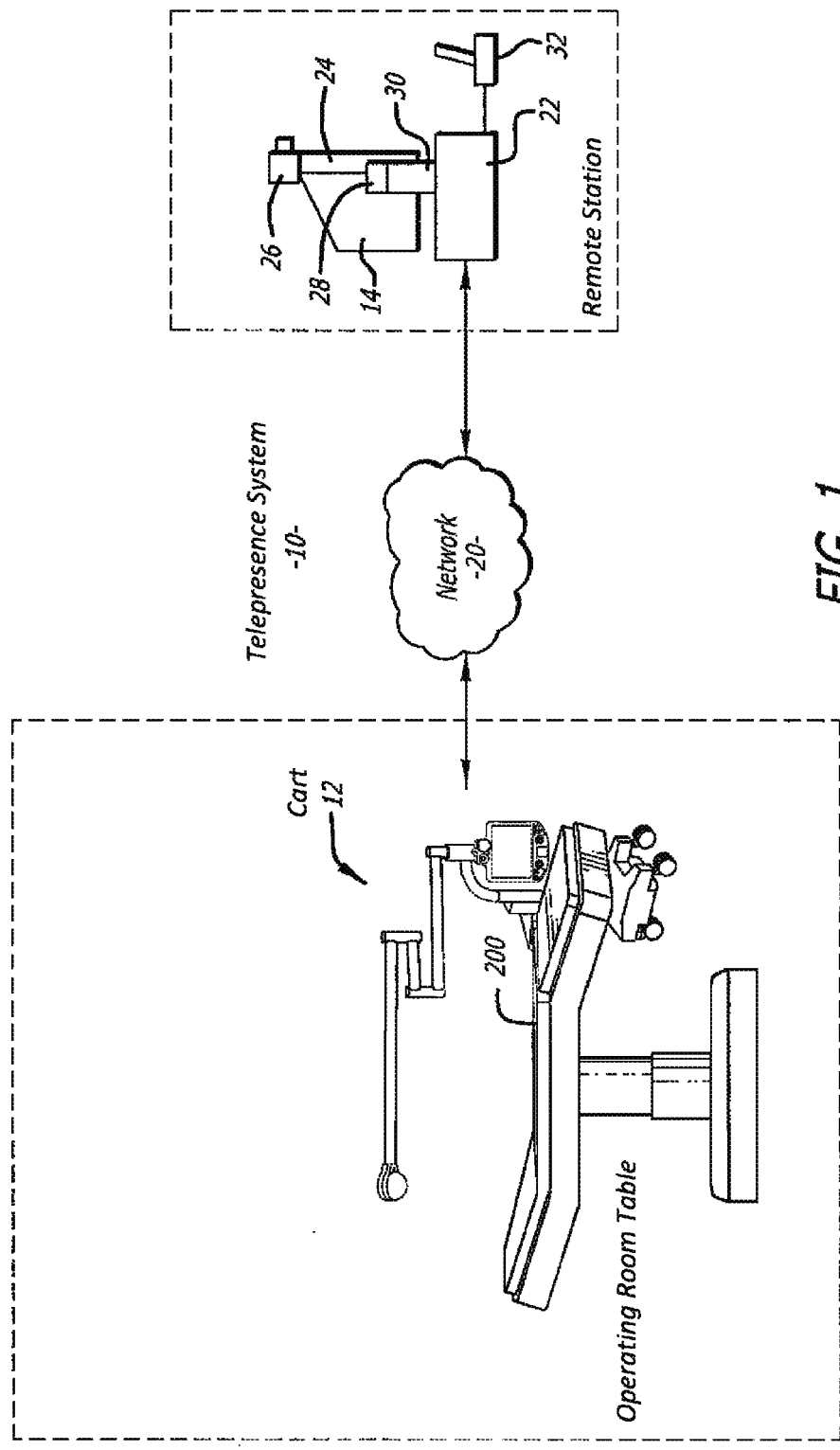
FIG. 1 is an illustration of a tele-presence system.
Figure 2:
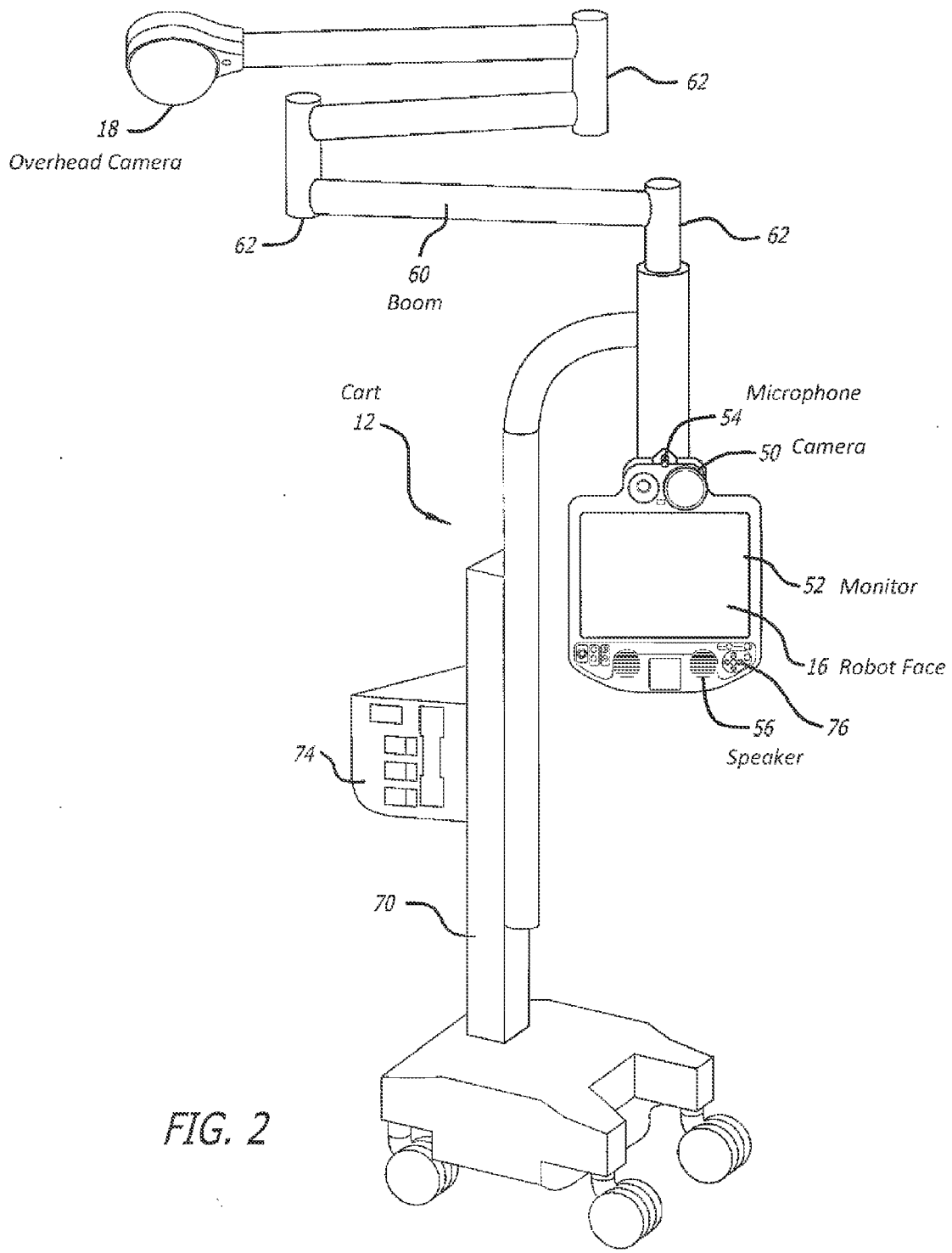
FIG. 2 is a perspective view of a cart of the system.
Figure 3:
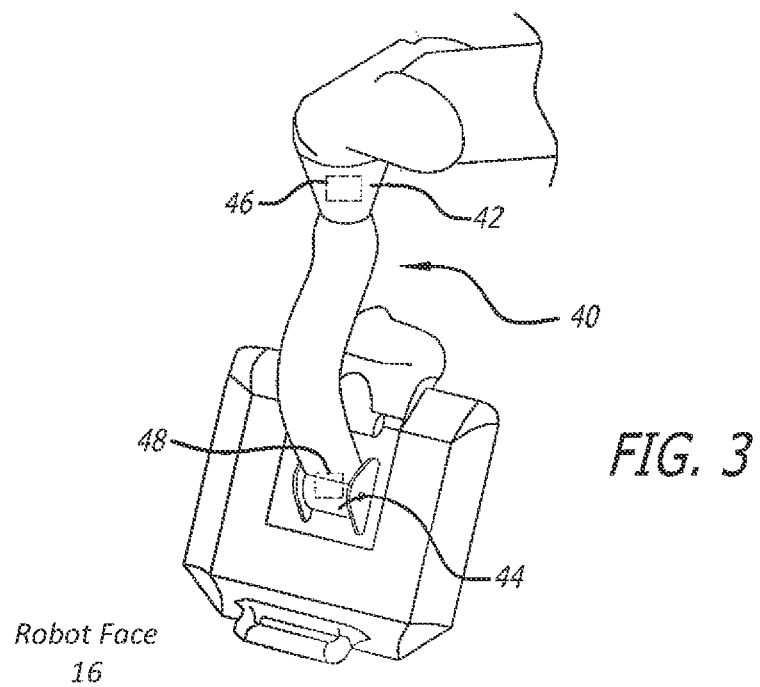
FIG. 3 is a rear view of an articulated arm and a robot face of the cart.

Referring to the drawings more particularly by reference numbers, FIGS. 1, 2 and 3 show a tele-presence system 10. The system 10 includes a cart 12 that is coupled to a remote control station 14. The cart 12 has a robot face 16 and an overhead camera 18. The remote control station 14 may be coupled to the cart 12 through a network 20. By way of example, the network 20 may be either a packet switched network such as the Internet, or a circuit switched network such as a Public Switched Telephone Network (PSTN) or other broadband system. Alternatively, the cart 12 may be coupled to the remote station 14 network thru a satellite.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the cart 12. Although only one remote control station 14 is shown, the system 10 may include a plurality of remote stations 14. In general any number of carts 12 may be coupled to any number of remote stations 14 or other carts 12. For example, one remote station 14 may be coupled to a plurality of carts 12, or one cart 12 may be coupled to a plurality of remote stations 14, or a plurality of carts 12. The system may include an arbitrator (not shown) that control access between the carts 12 and the remote stations 14.

As shown in FIG. 3, the cart 12 may include an articulated arm 40 that supports and can move the robot face 16. The articulated arm 40 may have active joints 42 and 44 that allow the robot face 16 to be panned and tilted, respectively. The active joints 42 and 44 may move in response to commands provided by the remote station. The joints 42 and 44 may contain position sensors 46 and 48, respectively, that provide positional feedback of the arm 40.

Referring to FIGS. 2 and 3, each robot face 16 includes a camera(s) 50, a monitor 52, a microphone(s) 54 and a speaker(s) 56. The robot camera 50 is coupled to the remote monitor 24 so that a user at the remote station 14 can view a video image captured by the robot camera 50. Likewise, the robot monitor 52 is coupled to the remote camera 26 so personnel at the surgical site may view the user of the remote station 14. The microphones 28 and 54, and speakers 30 and 56, allow for audible communication between the system operator and the personnel at the surgical site.

The overhead camera 18 may be coupled to a boom 60. The boom 60 may include a number of joints 62, either active or passive. The joints 62 may include positional sensors to provide feedback regarding the position of the overhead camera 18.

Figure 4:
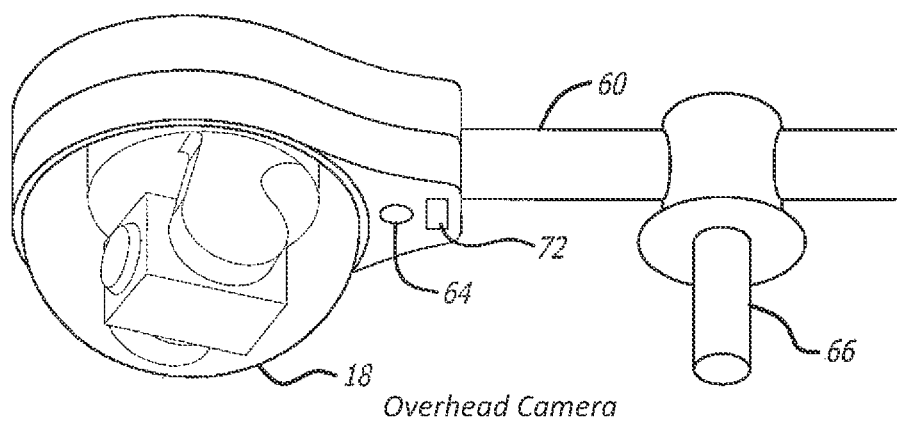
FIG. 4 is an enlarged perspective view of an overhead camera of the cart.

As shown in FIG. 4, the cart 12 may include an overhead microphone 64 and a detachable handle 66. The overhead microphone 64 may provide an alternative source of sound. The detachable handle 66 can be used to move the boom 60 and overhead camera 18. If the cart 12 is used in a sterile field, for example in an operating room, the handle 66 may be replaced with a sterile handle before each medical procedure to allow a surgeon within the sterile field to position the boom during a procedure.

Referring again to FIG. 2, the cart 12 may include a linear actuator 70 that can be remotely or locally actuated to vary the height of the robot face 16 and overhead camera 18. Varying the height allows the cart 12 to be rolled through doors and then actuated to move the face 16 and camera 18 to elevated positions. For example, the face 16 and camera 18 can be lowered to allow the cart 12 to be moved into an operating room. The camera 18 can then be raised to provide a desirable view over an operating table. The cart 12 may include a laser pointer 72 and/or directed lighting (not shown) located on the boom 60. The cart 12 may also include a local control panel 74 to move the articulated arm 40, actuator 70 and/or boom 60. The linear actuator 70 is also advantageous in moving the face 16 to be essentially at the same level as a person whether they are standing, sitting or lying in a prone position.

The robot face 16 may include a processor, hard disk drive and other circuits that enable the face 16 to function as a computer. The face 16 may include an input panel 76 that allows a user to provide input. By way of example, the operator of the remote station may provide one or more questions through the robot face 16, wherein a user of the cart provides answers through the input panel 76.

The system 10 may have certain components and software that are the same or similar to a robotic system provided by the assignee InTouch Technologies, Inc. of Goleta, Calif. under the name RP-7 and embodies a system described in U.S. Pat. No. 6,925,357, which is hereby incorporated by reference.

Figure 5:
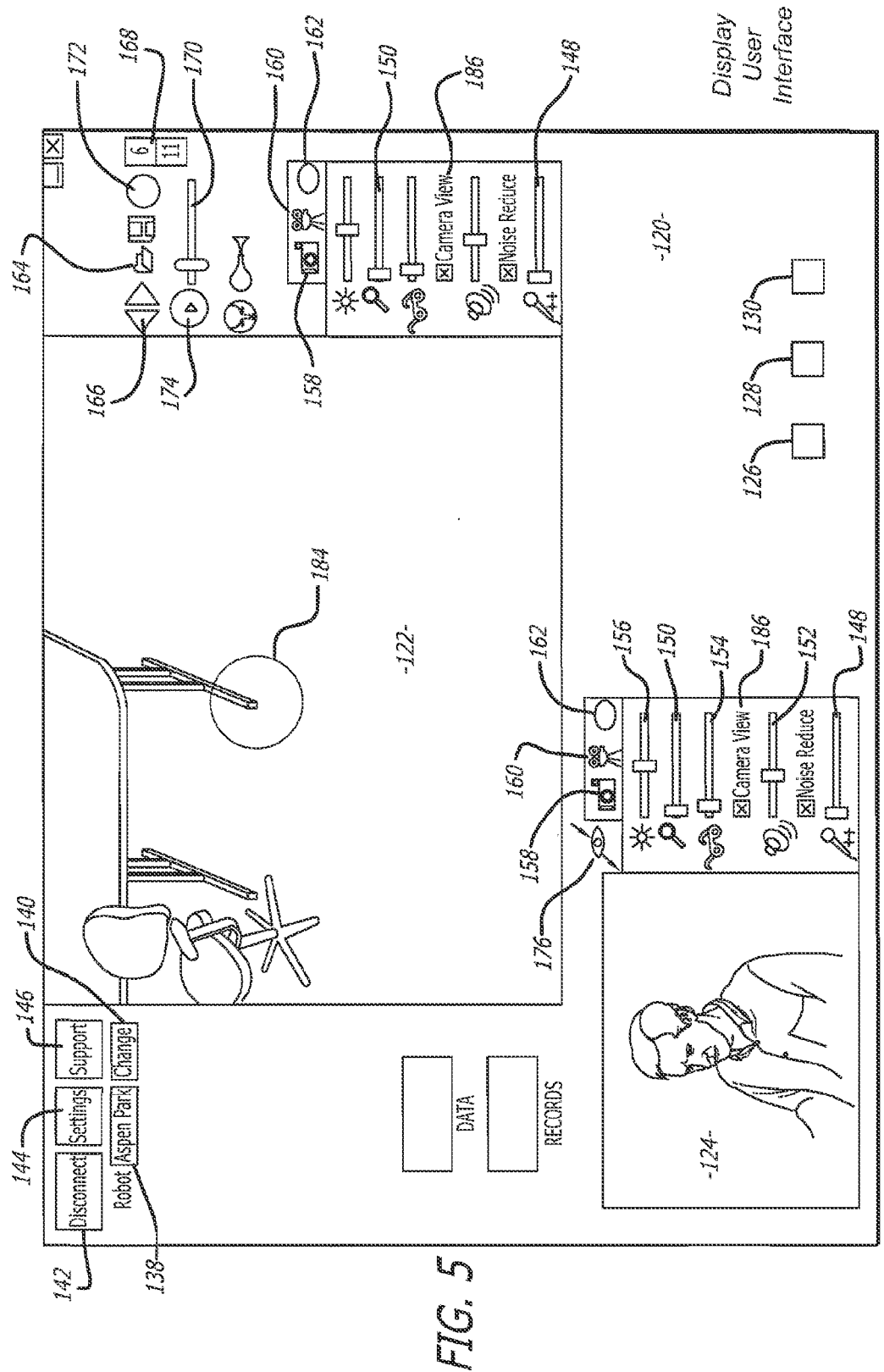
FIG. 5 is an illustration of a display user interface of a remote station.

FIG. 5 shows a display user interface ("DUI") 120 that can be displayed at the remote station 14. The DUI 120 may include a robot view field 122 that displays a video image captured by the robot camera and/or the overhead camera. The DUI 120 may also include a station view field 124 that displays a video image provided by the camera of the remote station 14. The DUI 120 may be part of an application program stored and operated by the computer 22 of the remote station 14.

Figure 6:
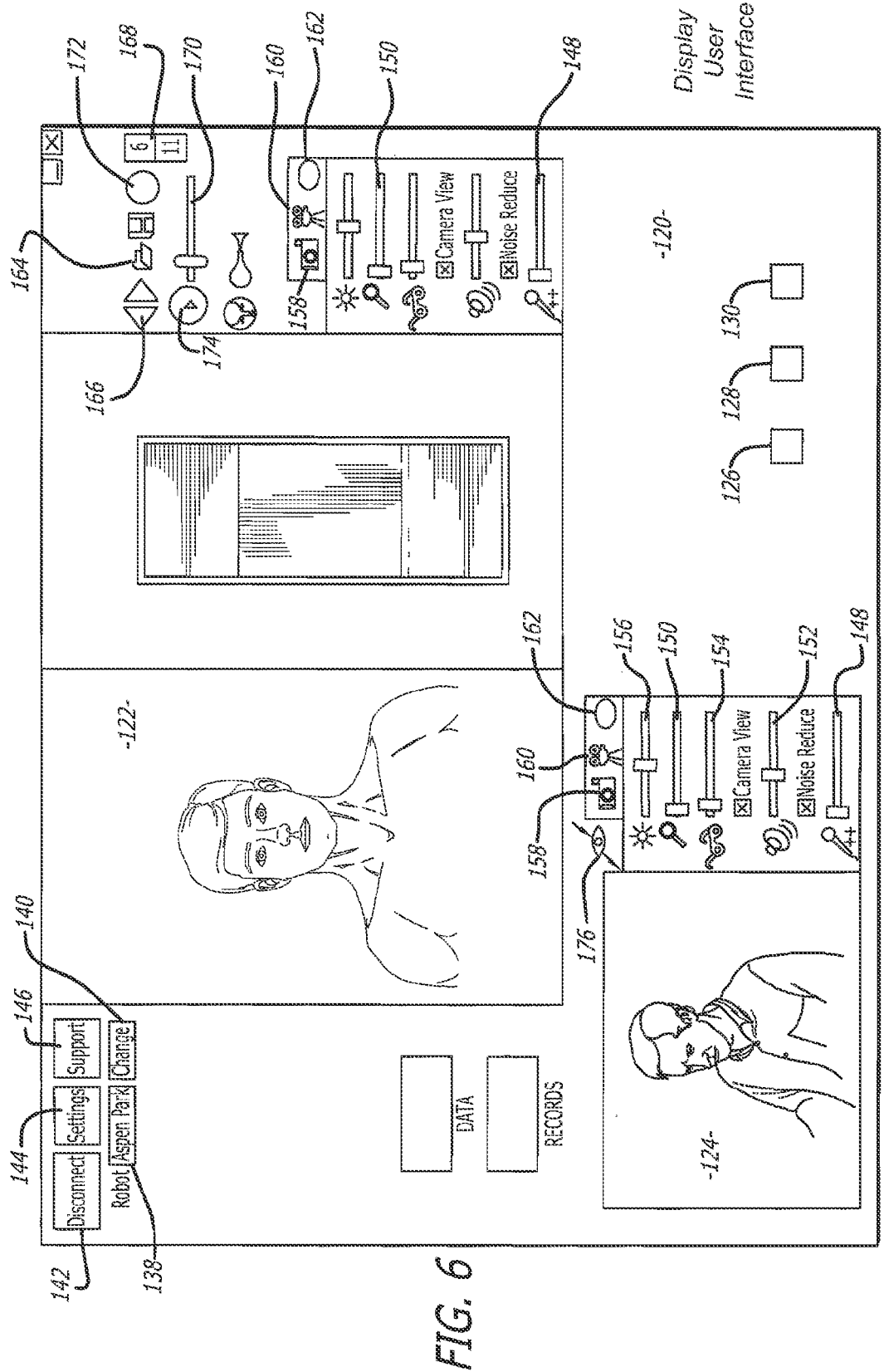
FIG. 6 is an illustration of the display user interface showing video images captured by a robot camera and an overhead camera being simultaneously displayed.

The DUI 120 may include a graphical switch 126 that allows the user to select between the video image provided by the robot camera and the video image provided by the overhead camera. The DUI 120 may also have a graphical switch 128 that allows the user to select the simultaneous display of the video images from the robot and overhead cameras as shown in FIG. 6. The video images from both cameras can be streamed to the remote station from the cart. The images can be merged by presenting a center rectangle of each image (e.g., 320×480 center area). A zoom or highlighting feature may be utilized by manipulating a cursor on either image. The system may also automatically pan a camera when the cursor is moved out of the displayed field of view.

The system may automatically present the video image from a camera that has an optimal view of an object. For example, the system may utilize pattern recognition techniques to determine which video image provides a more clear image of an object. The system may determine which camera is in closer proximity to an object and provide the image from the camera that is closer to the object. The system may utilize positional feedback from the cart to determine the proximity of the cameras relative to the object. The system may also have sensors, such as laser, sonar, etc. that can determine the proximity of the cameras to the object. The system may use the feedback and/or sensors to determine which camera is closer to an object.

The system may automatically move the cameras so that each camera is pointed to the same or substantially the same field of view. For example, if the robot face is pointed toward an object, the overhead camera can be automatically moved to capture a video image of the same object. Likewise, if the overhead camera is capturing a video image of an object, the robot face can be automatically moved to point toward the same object. This enhances the "presence" of the remote operator because they are facing the same object that the overhead camera is viewing.

The DUI 120 may have a graphical switch 130 that allows the user to switch between sound captured by the robot microphone or the overhead microphone. The system may automatically switch between microphones based on a characteristic(s) of the sound captured by the microphones. For example, the system may switch to the microphone that provides the highest aural clarity, or to the microphone that is in the closest proximity to a person or object generating the sound.

The DUI 120 may include a location display 138 that provides the location of the robot face. The CHANGE button 140 can be selected to change the default robot face in a new session. The CHANGE button 140 can be used to select and control a different robot face in a system that has multiple robot faces. The user can initiate and terminate a session by selecting box 142. The box 142 changes from CONNECT to DISCONNECT when the user selects the box to initiate a session. System settings and support can be selected through buttons 144 and 146.

Both the robot view field 122 and the station view field 124 may have associated graphics to vary the video and audio displays. Each field may have an associated graphical audio slide bar 148 to vary the audio level of a selected microphone and another slide bar 152 to vary the volume of the speakers.

The DUI 120 may have slide bars 150, 154 and 156 to vary the zoom, focus and brightness of a selected camera, respectively. A still picture may be taken at either the robot face or remote station by selecting one of the graphical camera icons 158. The still picture may be the image presented at the corresponding field 122 or 124 at the time the camera icon 158 is selected. Capturing and playing back video can be taken through graphical icons 160. A return to real time video can be resumed, after the taking of a still picture, captured video, or reviewing a slide show, by selecting a graphical LIVE button 162.

A still picture can be loaded from disk for viewing through selection of icon 164. Stored still images can be reviewed by selecting buttons 166. The number of the image displayed relative to the total number of images is shown by graphical boxes 168. The user can rapidly move through the still images in a slide show fashion or move through a captured video clip by moving the slide bar 170. A captured video image can be paused through the selection of circle 174. Play can be resumed through the same button 174. Video or still images may be dismissed from the active list through button 172. Video or still images may be transferred to the robot by selecting icon 176. For example, a doctor at the remote station may transfer an x-ray to the screen of the robot.

The system may provide the ability to annotate 184 the image displayed in field 122 and/or 124. For example, a doctor at the remote station may annotate some portion of the image captured by the robot face camera. The annotated image may be stored by the system. The system may also allow for annotation of images sent to the robot face through icon 176. For example, a doctor may send an x-ray to the robot face which is displayed by the robot screen. The doctor can annotate the x-ray to point out a portion of the x-ray to personnel located at the robot site. This can assist in allowing the doctor to instruct personnel at the robot site.

The display user interface may include graphical inputs 186 that allow the operator to turn the views of the remote station and remote cameras on and off.

Referring to FIG. 1, the cart 12 can be used in an operating room. By way of example, the boom 60 can be moved to place the overhead camera 18 above an operating table 200. The overhead camera 18 may be located above a sterile field. The robot face 16 may be placed adjacent to the sterile field. With such a configuration, personnel may conduct two-way video conferencing through the robot face 16. The overhead camera 18 may provide a more desirable view of the patient and operating procedure. This would allow a physician at the remote station to view the procedure and have a video conference to provide instructions, mentoring, etc. to personnel at the surgical site.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A tele-presence system, comprising:
   a cart, said cart includes a robot face that has a robot monitor, a robot camera, a robot speaker, a robot microphone, and an overhead camera distinct from said robot camera; and,
   a remote station that is coupled to said robot face and said overhead camera, said remote station includes a station monitor, a station camera, a station speaker and a station microphone, wherein at least one of said robot camera and said overhead camera can be controlled from the remote station.

2. The system of claim 1, wherein said remote station can display a video image from either said robot camera or said overhead camera.

3. The system of claim 1, wherein said remote station monitor simultaneously displays a video image from said robot camera and a video image from said overhead camera.

4. The system of claim 1, wherein said remote station determines an optimal view of an object and displays a video image from said robot camera or said overhead camera, whichever provides said optimal view.

5. The system of claim 1, wherein said robot camera automatically moves to capture a video image of a field of view that is at least substantially the same as a field of view of said overhead camera.

6. The system of claim 1, wherein said overhead camera automatically moves to capture a video image of a field of view that is at least substantially the same as a field of view of said robot camera.

7. The system of claim 1, wherein said cart includes an overhead microphone.

8. The system of claim 7, wherein said remote station includes an input that allows a user to switch between said robot microphone and said overhead microphone.

9. The system of claim 7, wherein said sound generated by said station speakers is automatically switched between said robot microphone or said overhead microphone based on a characteristic of sound captured by said robot and overhead microphones.

10. The system of claim 1, wherein said cart includes an actuator that can vary a height of said robot face.

11. The system of claim 1, wherein said cart includes an articulated arm that is coupled to and can move said robot face, and a boom that is coupled to said overhead camera.

12. The system of claim 11, wherein said robot face includes an input panel and can be operated as a computer.

13. The system of claim 11, wherein said articulated arm and said boom include position sensors.

14. The system of claim 11, wherein further comprising a laser pointer attached to said boom.

15. The system of claim 11, wherein said cart boom includes a detachable handle.

16. A method for remotely viewing a field of view, comprising:
   moving a cart, the cart includes a robot face that has a robot monitor, a robot camera, a robot speaker, a robot microphone, and an overhead camera distinct from said robot camera;
   transmitting to a remote station a video image captured by the robot camera or a video image captured by the overhead camera, the remote station includes a station monitor, a station camera, a station speaker and a station microphone; and,
   controlling at least one of said robot camera and said overhead camera in response to a command received from the remote station.

17. The method of claim 16, wherein the video images captured by the robot and overhead cameras are both transmitted to the remote station.

18. The method of claim 17, wherein the remote station monitor simultaneously displays the video image from the robot camera and the video image from the overhead camera.

19. The method of claim 16, wherein the remote station determines an optimal view of an object and displays a video image from robot camera or the overhead camera, whichever provides the optimal view.

20. The method of claim 16, further comprising automatically moving the robot camera to capture a video image of a field of view that is at least substantially the same as a field of view of the overhead camera.

21. The method of claim 16, further comprising automatically moving the overhead camera to capture a video image of a field of view that is at least substantially the same as a field of view of the robot camera.

22. The method of claim 16, further comprising capturing sound with an overhead microphone of the cart.

23. The method of claim 22, further comprising selecting an input to switch between the robot microphone and the overhead microphone.

24. The method of claim 22, further comprising automatically switching between the robot microphone and the overhead microphone based on a characteristic of the sound captured by the robot and overhead microphones.

25. The method of claim 16, further comprising varying a height of the robot face.

26. The method of claim 25, wherein the robot face is moved in two degrees of freedom.

27. The method of claim 16, wherein the cart is moved within an operating room.

28. The method of claim 27, further comprising moving the overhead camera above a sterile field.

29. The method of claim 16, further comprising entering input into the robot face.

30. The method of claim 16, further comprising replacing a detachable handle of the cart.

* * * * *